United States Patent
Connor et al.

(10) Patent No.: US 9,228,170 B2
(45) Date of Patent: Jan. 5, 2016

(54) CELL PROGRAMMING

(75) Inventors: Bronwen Jane Connor, North Shore City (NZ); Mirella Dottori, Victoria (AU); Christof Maucksch, Auckland (NZ)

(73) Assignees: AUCKLAND UNISERVICES LIMITED, Auckland (NZ); THE UNIVERSITY OF MELBOURNE, Victoria (AU)

( * ) Notice: Subject to any disclaimer, the term of this patent is extended or adjusted under 35 U.S.C. 154(b) by 0 days.

(21) Appl. No.: 13/576,778

(22) PCT Filed: Feb. 4, 2011

(86) PCT No.: PCT/NZ2011/000010
§ 371 (c)(1),
(2), (4) Date: Aug. 2, 2012

(87) PCT Pub. No.: WO2011/096825
PCT Pub. Date: Aug. 11, 2011

(65) Prior Publication Data
US 2012/0301965 A1      Nov. 29, 2012

(30) Foreign Application Priority Data
Feb. 5, 2010   (NZ) ........................... 583115

(51) Int. Cl.
*C12N 15/85*     (2006.01)
*C12N 5/0797*    (2010.01)

(52) U.S. Cl.
CPC .......... *C12N 5/0623* (2013.01); *C12N 2500/34* (2013.01); *C12N 2501/065* (2013.01); *C12N 2501/11* (2013.01); *C12N 2501/115* (2013.01); *C12N 2501/385* (2013.01); *C12N 2501/60* (2013.01); *C12N 2501/602* (2013.01); *C12N 2501/91* (2013.01); *C12N 2506/1307* (2013.01); *C12N 2510/00* (2013.01)

(58) Field of Classification Search
None
See application file for complete search history.

(56) References Cited

U.S. PATENT DOCUMENTS

2009/0191159 A1*   7/2009   Sakurada et al. ............ 424/93.7
2012/0220034 A1*   8/2012   Ahlfors et al. .............. 435/375

FOREIGN PATENT DOCUMENTS

WO    2010/052904    5/2010

OTHER PUBLICATIONS

Vierbuchen et al. "Direct conversion of fibroblasts to functional neurons by defined factors." Nature. 2010; 463(7284): 1035-1041.*
Kim et al. "Direct reprogramming of mouse fibroblasts to neural progenitors." Proc. Natl. Acad. Sci. (2011) USA 108: pp. 7838-7843.*
Kim (b) et al. "Generation of Human Induced Pluripotent Stem Cells by Direct Delivery of Reprogramming Proteins." Cell Stem Cell. Jun. 5, 2009; 4(6): 472-476.*
Park et al. "SOX2 has a crucial role in the lineage determination and proliferation of mesenchymal stem cells through Dickkopf-1 and c-MYC." Cell Death and Differentiation (2012) 19, 534-545.*
Carpenter et al. "Generation and Transplantation of EGF-Responsive Neural Stem Cells Derived from GFAP-hNGF Transgenic Mice." Experimental Neurology (1997) 148, 187-204.*
Yamanaka et al. "Induction of pluripotent stem cells from mouse fibroblasts by four transcription factors." Cell Prolif. 2008,41: pp. 51-56.*
Wachs et al. "High efficacy of clonal growth and expansion of adult neural stem cells." Lab Invest. Jul. 2003;83(7):949-62.*
Wernig, M. et al., Neurons derived from reprogrammed fibroblasts functionally integrate into the fetal brain and improve symptoms of rats with Parkinson's disease, Proceedings of the National Academy of Sciences of the USA, 2008, vol. 105, No. 15, pp. 5856-5861.
Vierbuchen, T. et al., Direct conversion of fibroblasts to functional neurons by defined factors, Nature, 2010, vol. 463, No. 7284 (Epub Jan. 27), pp. 1035-1041.
Zhu, X-Q. et al., Transient in vitro epigenetic reprogramming of skin fibroblasts into multipotent cells, Biomaterials, 2010, vol. 31, No. 10 (Epub Dec. 30, 2009), pp. 2779-2787.
Ma, W. et al., Reprogramming retinal pigment epithelium to differentiate toward retinal neurons with Sox2, Stem Cells, 2009, vol. 27, No. 6, pp. 1376-1387.
Azuma, N. et al., Transdifferentiation of the retinal pigment epithelia to the neural retina by transfer of the Pax6 transcriptional factor, Human Molecular Genetics, 2005, vol. 14, No. 8, pp. 1059-1068.
Fong, C.-Y. et al., Teratomas from pluripotent stem cells: a clinical hurdle, Journal of Cellular Biochemistry, 2010, vol. 111, No. 4, pp. 769-781.
Guo, Z. et al., Expression of Pax6 and Sox2 in adult olfactory epithelium, The Journal of Comparative Neurology, 2010, vol. 518, No. 21, pp. 4395-4418.
International Search Report for PCT/NZ2011/000010, dated Apr. 27, 2011.

* cited by examiner

*Primary Examiner* — Thaian N Ton
*Assistant Examiner* — Titilayo Moloye
(74) *Attorney, Agent, or Firm* — Wenderoth, Lind & Ponack, L.L.P.

(57) ABSTRACT

The present invention is concerned with methods for reprogramming of mammalian somatic cells and in particular to reprogramming of mature mammalian somatic cells into multi-potent precursor cells.

9 Claims, 10 Drawing Sheets

A

B

C

SEQUENCE LISTING

```
<160> NUMBER OF SEQ ID NOS: 18

<210> SEQ ID NO 1
<211> LENGTH: 22
<212> TYPE: DNA
<213> ORGANISM: Homo sapiens

<400> SEQUENCE: 1
gtgagaggca acctggagaa tt                                              22

<210> SEQ ID NO 2
<211> LENGTH: 22
<212> TYPE: DNA
<213> ORGANISM: Homo sapiens

<400> SEQUENCE: 2
cattcctaga agggcaggca cc                                              22

<210> SEQ ID NO 3
<211> LENGTH: 21
```

```
<212> TYPE: DNA
<213> ORGANISM: Homo sapiens

<400> SEQUENCE: 3
cagtacagcc ccatctccaa c                                              21

<210> SEQ ID NO 4
<211> LENGTH: 19
<212> TYPE: DNA
<213> ORGANISM: Homo sapiens

<400> SEQUENCE: 4
gcgggcaagt acatgctga                                                 19

<210> SEQ ID NO 5
<211> LENGTH: 21
<212> TYPE: DNA
<213> ORGANISM: Homo sapiens

<400> SEQUENCE: 5
gccgagtgga aactttgtc g                                               21

<210> SEQ ID NO 6
<211> LENGTH: 22
<212> TYPE: DNA
<213> ORGANISM: Homo sapiens

<400> SEQUENCE: 6
gcagcgtgta cttatccttc tt                                             22

<210> SEQ ID NO 7
<211> LENGTH: 19
<212> TYPE: DNA
<213> ORGANISM: Homo sapiens

<400> SEQUENCE: 7
cgcgggttcc tgctgattt                                                 19

<210> SEQ ID NO 8
<211> LENGTH: 21
<212> TYPE: DNA
<213> ORGANISM: Homo sapiens

<400> SEQUENCE: 8
cggggttctt gagttcagtc t                                              21

<210> SEQ ID NO 9
<211> LENGTH: 20
<212> TYPE: DNA
<213> ORGANISM: Homo sapiens

<400> SEQUENCE: 9
tcacagcgga gtgaatcagc                                                20

<210> SEQ ID NO 10
<211> LENGTH: 22
<212> TYPE: DNA
<213> ORGANISM: Homo sapiens

<400> SEQUENCE: 10
tatcgttggt acagaccccc tc                                             22

<210> SEQ ID NO 11
```

```
<211> LENGTH: 19
<212> TYPE: DNA
<213> ORGANISM: Homo sapiens

<400> SEQUENCE: 11
gaatggactt tggaagcag                                                    19

<210> SEQ ID NO 12
<211> LENGTH: 20
<212> TYPE: DNA
<213> ORGANISM: Homo sapiens

<400> SEQUENCE: 12
aactggttag gatagataca                                                   20

<210> SEQ ID NO 13
<211> LENGTH: 21
<212> TYPE: DNA
<213> ORGANISM: Homo sapiens

<400> SEQUENCE: 13
gcacagaaag tcatcaaagc c                                                 21

<210> SEQ ID NO 14
<211> LENGTH: 21
<212> TYPE: DNA
<213> ORGANISM: Homo sapiens

<400> SEQUENCE: 14
ttgatctggg tcatgcagtt g                                                 21

<210> SEQ ID NO 15
<211> LENGTH: 25
<212> TYPE: DNA
<213> ORGANISM: Homo sapiens

<400> SEQUENCE: 15
ttctcagaga atgtgtgtgc agagt                                             25

<210> SEQ ID NO 16
<211> LENGTH: 23
<212> TYPE: DNA
<213> ORGANISM: Homo sapiens

<400> SEQUENCE: 16
ggtcagacac ttggcagaag atg                                               23

<210> SEQ ID NO 17
<211> LENGTH: 20
<212> TYPE: DNA
<213> ORGANISM: Homo sapiens

<400> SEQUENCE: 17
gctggcatct gctctattcc                                                   20

<210> SEQ ID NO 18
<211> LENGTH: 20
<212> TYPE: DNA
<213> ORGANISM: Homo sapiens

<400> SEQUENCE: 18
atgaagcaat cctccctcct                                                   20
```

CELL PROGRAMMING

FIELD OF THE INVENTION

The present invention relates to reprogramming of mammalian somatic cells and in particular to reprogramming of mature mammalian somatic cells.

The invention has been developed primarily for use as a method of reprogramming a mature human fibroblast into a lineage-specific neural precursor cell and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

Embryonic stem cells, derived from the inner cell mass of mammalian blastocysts, have the capability to grow indefinitely while maintaining the ability to generate all cell and tissue types in the body (pluripotency). These properties have lead to expectations that human embryonic stem cells (hESCs) might be useful to treat patients with various diseases and injuries, thereby revolutionizing regenerative medicine.

Cell transplantation therapy using stem cells may offer a viable treatment strategy for patients with brain disease or injury, such as Parkinson's disease, Huntington's disease, stroke or spinal cord injury by providing new cells to replace those lost through disease. However, the clinical application of hESCs faces difficulties regarding ethical concerns relating to the use of embryos, as well as instances of tissue rejection after implantation due to immunological incompatibility between patient and donor cells.

One way to circumvent these issues is to artificially derive an embryonic stem cell-like (pluripotent) cell from a mature somatic cell by inducing a "forced" expression of certain genes. These artificially derived embryonic stem cell-like cells are known as induced pluripotent stem (iPS) cells and are believed to be identical to embryonic stem cells in many respects (Hochedlinger, K. & Plath, K; (2009) Development 136, 509-523). The generation of iPS cells from mature somatic cells, such as fibroblast cells obtained directly from the patient, prevents therapeutic concerns regarding ethics and/or tissue rejection, and may potentially provide the optimal cell source for regenerative medicine.

iPS cells were first generated by Yamanaka and colleagues in 2006 from mouse fibroblast cells (Cell 126, 663-676). The method of deriving iPS cells traditionally involves the transfection of certain embryonic stem cell-associated genes into non-pluripotent cells, such as mature fibroblasts. Transfection is usually achieved-through viral vectors, such as retroviruses. Yamanaka and colleagues ((2006) Cell 126, 663-676) initially identified 4 key genes essential for the production of pluripotent stem cells: Oct-3/4, Sox2, c-Myc and Klf4. Additional studies demonstrated the requirement of Nanog as a another major determinant of cellular pluripotency (Okita, K., Ichisaka, T. & Yamanaka, S. (2007) Nature 448, 313-317; Wernig, M. et al. (2007) Nature 448, 318-324; and Maherali, N. et al. (2007) Cell Stem Cell 1, 55-70). In 2007, two independent research groups generated iPS cells from human cells (Takahashi, K. et al. (2007) Cell 131, 861-872; and Yu, J. et al. (2007) Science 318, 1917-1920). Applying the same principles used earlier in mouse cells, Yamanaka and colleagues (Takahashi, K. et al. (2007) Cell 131, 861-872) successfully transformed human fibroblasts into pluripotent stem cells using the same 4 pivotal genes Oct-3/4, Sox2, c-Myc and Klf4 in a retroviral transfection system. Thomson and colleagues (Yu, J. et al. (2007) Science 318, 1917-1920) used Oct4, Sox2, Nanog and Lin28 using a lentiviral transfection system. The exclusion of c-Myc in these experiments was based on evidence that c-Myc is oncogenic and is not necessary to promote cellular pluripotency.

The use of neural precursor cells derived from hESCs or iPS cells bears great therapeutic potential for the treatment of neurological disorders and injuries such as Parkinson's disease, Huntington's disease, stroke or spinal cord injury through the generation of replacement neural cells. Currently cell transplantation therapy of neural precursor cells requires in vitro differentiation of the neural precursor cells from hESCs or iPS cells.

As reported, both hESCs and iPS cells can be efficiently differentiated into neural precursor cells, using either spontaneous or factor-induced differentiation protocols. Those neural precursor cells are capable of giving rise to neuronal and glial cells both in culture and in vivo (Wernig, M. et al. (2009) Proceeding of the National Academy of Science 105, 5856-5861; Dottori, M. & Pera, M. F. (2008) Methods Mol Biol 438, 19-30; Reubinoff, B. E. et al. (2001) Nature Biotechnology 19, 1134-1140; Reubinoff, B. E., Pera, M. F., Fong, C.-Y., Trounson, A. & Bongso, (2000) Nature Biotechnology 18, 399-404; Itsykson, P. et al. (2005) Molecular and Cellular Neuroscience 30, 24-36; Pera, M. F. et al. (2004) Journal of Cell Science 117, 1269-1280).

Previous work, including that of the inventors, demonstrates that hESC-derived or iPS-derived neural precursor cells survive transplantation into the injured adult rodent brain and differentiate towards both neuronal and glial cell fates—some studies demonstrating recovery of function (i.e: Bjorklund, Sanchez-Pernaute et al. (2002) PNAS 99: 2344-2349; Kim, Auerbach et al. (2002) Nature 418: 50-56; Ben-Hur, Idelson et al. (2004) Stem Cells 22(7): 1246-1255, Dinsmore, Ratliff et al. (1996) Cell Transplantation 5(2): 131-143; Dihne, Bernreuther et al. (2006) Stem Cells 24(6): 1458-1466; Riess, Molcanyi et al. (2007) Journal of Neurotrauma 24(1): 216-225; Song, Lee et al. (2007) Neuroscience Letters 423(1): 58-61; Aubry, Bugi et al. (2008) PNAS; Dali, Zhi-Jian et al. (2008) Stem Cells 26(1): 55-63; Hatami, Mehrjardi et al. (2009) Cytotherapy 11(5): 618-630; Hicks, Lappalainen et al. (2009) European Journal of Neuroscience 29(3): 562-574, Vazey et al. (2010) Cell Transplantation, 19; 1055-1062).

However, the formation of tumours, such as teratomas, following transplantation of hESC-derived neural precursor cells has been observed in a number studies (Roy, N. S. et al. (2006) Nat Med 12, 1259-1268; Erdo, F. et al. (2003) J Cereb Blood Flow Metab 23, 780-785 (2003); Hedlund, E. et al. (2007) Stem Cell 25, 1126-1135; Pruszak, J., Sonntag, K.-C., Aung, M. H., Sanchez-Pernaute, R. & Isacson, O. (2007) Stem Cells 25, 2257-2268; Bjorklund, L. M. et al. (2002) Proceeding of the National Academy of Science 99, 2344-2349; (Riess, Molcanyi et al. (2007) Journal of Neurotrauma 24(1): 216-225; Aubry, Bugi et al. (2008) PNAS; Vazey et al. (2010) Cell Transplantation, 19; 1055-1062)., and was noted by Wernig and colleagues (2009) Proceeding of the National Academy of Science 105, 5856-5861) in a recent study in which iPS cell-derived neural precursors were transplanted into a 6-OHDA lesion model of Parkinson's disease. The formation of teratomas is thought to result from a proportion of the transplanted cells retaining an undifferentiated (i.e. pluripotent) state. Accordingly, teratoma formation following transplantation of hESC- or iPS cell-derived neural precursor cells presents a major obstacle for the clinical application of stem cell therapy, as tumour formation as a clinical result of cell transplantation therapy in human patients is unacceptable.

In light of the limitations shown for hESCs and iPS cells (including ethical considerations, tissue rejection and tumourgenicity), a need for a source of cells for central nervous system (CNS) transplantation therapy exists.

As said above, reprogramming mature somatic cells, as demonstrated by the generation of iPS cells, removes ethical concerns raised over the use of hESCs and also allows for the transplantation of cells obtained from the patient's own body (autologous transplantation), addressing issues of tissue rejection. However, the use of iPS cells does not address the concerns of tumour formation associated in transplantation therapy resulting from co-transplantation of a proportion of non-committed pluripotent cells.

It is an object of the present invention to overcome or ameliorate at least one of the disadvantages of the prior art, or to provide a useful alternative.

SUMMARY OF THE INVENTION

It has unexpectedly been found that mature mammalian somatic cells such as mature mammalian fibroblasts, can be reprogrammed directly into multi-potent lineage-specific precursor cells. This reprogramming does not require reprogramming of the cell's genetic profile to a pluripotent state, such as is required for induced pluripotent stem (iPS) cells, and shows that delivering certain combinations of lineage-specific transcription factors to the somatic cells reprograms the somatic cells into a committed (i.e. lineage specific) multi potent precursor cell.

The inventors surprisingly found that, for example, delivering the transcription factors Sox2 and Pax6 to mature human fibroblasts reprograms the fibroblasts to a multi-potent lineage-specific neural precursor cell which expresses the neural precursor cell and immature neuronal markers Pax6, Sox2, Hes1, Sox3, Ngn2 and Mash1.

Accordingly, in a first aspect the present invention relates to a method of reprogramming a mature mammalian somatic cell into a reprogrammed multi-potent lineage-specific precursor cell, said method comprising the steps of:
a) delivering one or more factors to said somatic cell, wherein said one or more factors determine the lineage specificity of said precursor cell; and
b) culturing said somatic cell under conditions permissive to the culture of said lineage-specific precursor cell.

Preferably the mature mammalian somatic cell is a mature mammalian fibroblast. Fibroblasts can be obtained from any source such as, for example lung fibroblasts, kidney fibroblasts, cardiac fibroblasts, stromal fibroblasts, foreskin fibroblasts and the like, when used in the methods of the present invention. However, as will be appreciated, mature human dermal fibroblasts provide a convenient source of somatic cells. Fibroblasts may be conveniently obtained from a commercial source or, if desired, isolated from tissue sources using well established and documented laboratory techniques and equipment.

In some preferred embodiments the mature mammalian somatic cell is a cell from a patient suffering from a neurological disorder or injury in which tissue regeneration is a component of healing and the reprogrammed multi-potent lineage-specific precursor cell is a disease-specific reprogrammed multi-potent lineage-specific precursor cell.

In some preferred embodiments the reprogrammed multi-potent, lineage-specific precursor cell is a multi-potent neural precursor cell. Preferably, the multi-potent neural precursor cell expresses at least one neural cell lineage marker selected from the group consisting of Pax6, Sox2, Hes 1, Hes 5, Sox1, Sox3, Mash 1/Ash1 1 and neurogenin 2.

Preferably the step of delivering one or more factors to the somatic cell preferably includes the delivery of the one or more factors via protein transduction or via protein expression from non-viral or viral vectors, using techniques well known in the art.

Preferably, the one or more factors are selected from proteins such as transcription factors, nucleic acids encoding the transcription factors, small molecules capable of influencing the amount of the transcription factor present in the somatic cell, or any combinations thereof. More preferably, the factors are the transcription factors Sox2 and Pax6 or any known transcription factors which, alone or in combination, are capable of producing multi-potent neural precursor cells in a method according to the invention.

Typically, the step of culturing the somatic cell includes culturing the cell in any medium capable of supporting growth of precursor cells, such as for example stem cell medium.

Preferably the medium is supplemented with a chromatin modifying agent capable of facilitating the reprogramming of the somatic cell. The chromatin modifying agent may be selected from agents promoting acetylation of chromatin, inhibiting deacetylation of chromatin, altering histone methylation states within chromatin or leading to DNA demethylation within chromatin. Preferably the chromatin modifying agent is valproic acid. Even more preferable is valproic acid at a concentration of 1 μM.

In a second aspect the present invention relates to a reprogrammed multi-potent lineage-specific precursor cell produced by a method according to the first aspect. The precursor cell is preferably a multi-potent neural precursor cell.

DEFINITIONS

In the context of this specification the following terms are defined as follows:
"comprising"
Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".
"mature"
In so far as this term refers to cells it is to be construed to refer to cells which have reached their final differentiation state, i.e. cells which no longer have a potential to further differentiate. Such cells can be found at various developmental stages including embryonal, post natal or adult stages, but, as will be appreciated, are most conveniently sourced from adults.
"neural"
In so far as this term refers to cells of the nervous system it is to be construed to include "neuronal" and "glial" cells
"lineage"
In so far as this term refers to cell lineages, a lineage is a genealogic pedigree of cells related through mitotic division.
"lineage-specific"
In so far as this term refers to cells, it refers to the differentiation state to which a cell has become committed.
"precursor cell"
In so far as this term refers to cells, it refers to a cell capable of differentiating into a number of cell and/or tissue types of a cell lineage.

"pluripotent"

In so far as this term refers to cells, it refers to a cell capable of differentiating into cell and/or tissue types of all cell lineages, excluding extra embryonic cell and/or tissue types.

"multi-potent"

In so far as this term refers to cells, it refers to a cell capable of differentiating into of cell and/or tissue types of multiple but not all cell lineages.

"induced multi-potent neural precursor (iMNP) cell"

This term refers to a type of multi-potent precursor cell which has been artificially derived from a non-pluripotent or multi-potent source, typically a mature somatic cell, by inducing expression of certain genes characteristic for cells of neural lineage. Therefore, iMNP cells are only capable of differentiating into neural cell and/or tissue types.

BRIEF DESCRIPTION OF THE DRAWINGS

A preferred embodiment of the invention will now be described, by way of example only, with reference to the accompanying figures in which:

FIGS. 3(B) and (C) are fluorescence activated cell sorting (FACs) blots showing the analysis of (B) control and (C) PE protein transduced human dermal fibroblasts (HDF) using the ProDeliverIn system at a PE and ProDeliverIn ratios of 1:2. FIG. 3(C) demonstrates that a transduction efficiency of approximately 50% can be achieved.

FIGS. 5(B) and (C) are fluorescence activated cell sorting (FACs) blots showing the analysis of (B) control and (C) eGFP transfected HDF cells using the Lipofectamine LTX gene delivery agent at a ratio of 6:1 (v/m). FIG. 5(C) demonstrates that a transduction efficiency of approximately 12% can be achieved.

FIG. 6(A) demonstrates mature HDF cells in culture prior to Sox2/Pax6 plasmid transfection. FIG. 6(B) demonstrates the formation of iMNP colonies approximately 30 days following Sox2/Pax6 plasmid co-transfection using the Lipofectamine LTX gene delivery agent. FIGS. 6(C to E) represent the formation of secondary colonies following the dissociation of primary colonies. FIG. 6(C) is an image of secondary colony formation 1 day following dissociation of primary colonies. FIG. 6(D) is an image of secondary colonies 4 days following dissociation of primary colonies. FIG. 6(E) is an image of a secondary colony 10 days following dissociation of primary colonies. FIG. 6(F) is a graph demonstrating the number of iMNP colonies of a given size (diameter) as a percentage of the total colonies measured prior to dissociation (pre dins), and 6, 10 and 14 days following dissociation. Colonies measured prior to dissociation represent primary colonies. Colonies measured after dissociation represent secondary colony formation. The graph demonstrates the formation of secondary colonies by 6 days following dissociation. The size of secondary colonies generated following dissociation is increased compared to primary colonies.

PREFERRED EMBODIMENT OF THE INVENTION

Cell transplantation therapy using stem cells may offer a viable treatment strategy for patients with brain disease or injury, such as Parkinson's disease, Huntington's disease, stroke or spinal cord injury, by providing new cells to replace those lost through disease. Embryonic stem cells have the capability to grow indefinitely while maintaining the ability to generate all cell types in the body. These properties have lead to expectations that human embryonic stem cells might be useful to treat patients with various diseases or injuries, including brain injury and disease, thereby revolutionising regenerative medicine.

Figure 1:
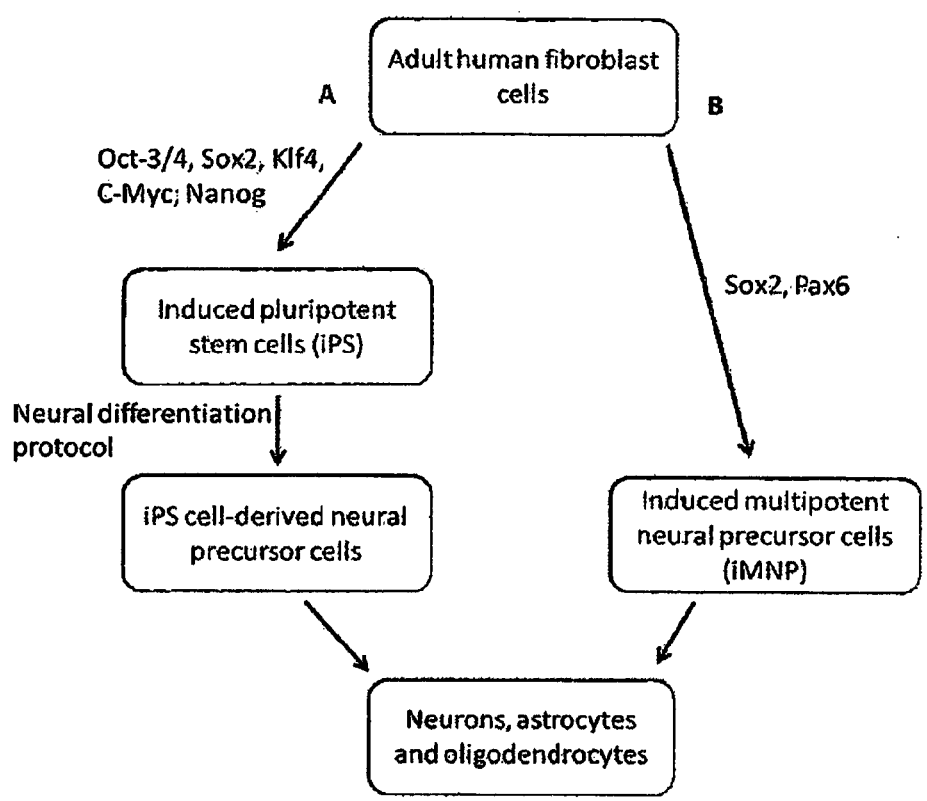
FIG. 1 is a flowchart comparing the steps (A) necessary to produce neurons, astrocytes, and oligodendrocytes from neural precursor cells derived from induced pluripotent stem (iPS) cells as known in the art, with the steps (B) necessary to produce these cells from induced multi-potent neural precursor (iMNP) cells derived from a mature human fibroblast in a method according to the invention.

However, the clinical application of human embryonic stem cells faces difficulties regarding the use of embryos, as well as issues of tissue rejection after implantation due to immunological incompatibility between patient and donor cells. One way to circumvent these issues is to artificially derive a stem-like cell from mature somatic cells, such as fibroblast cells, by inducing a "forced" expression of certain genes (FIG. 1A). These artificially derived stem cells are known as induced pluripotent stem cells (iPS cells) and are believed to be identical to embryonic stem cells in many respects. As such, the generation of iPS cells from mature somatic cells, such as fibroblast cells, obtained directly from the patient prevents therapeutic concerns regarding ethics and tissue rejection, and may potentially provide the optimal cell source for regenerative medicine.

In order for embryonic stem cells or iPS cells to be used for the treatment of brain disease or injury, they must first be directed to form neural (brain) precursor cells prior to transplantation. However, results from the inventors' research and that of others has demonstrated that transplantation of neural precursor cells derived from either embryonic stem cells or iPS cells can lead to the formation of tumours due to the contamination of a population of pluripotent cells still uncommitted to a specific cell lineage.

The present invention relates to reprogramming of mammalian somatic cells by delivering one or more selected factors to the cells which determine the lineage specificity of the reprogrammed cell. In one or more preferred embodiments the present invention provides the use of mature mammalian fibroblasts in the reprogramming methods described. Fibroblasts are found within fibrous connective tissue and are associated with the formation of collagen fibres and ground substance of connective tissue. While mammalian fibroblasts from any source such as, for example lung fibroblasts, kidney fibroblasts, cardiac fibroblasts, stromal fibroblasts, foreskin fibroblasts and the like, may be used in the methods of the present invention, mature mammalian dermal fibroblasts provide a convenient source of somatic cells. Such fibroblasts can be conveniently obtained from a commercial source or, if desired, may be isolated from various tissues using well established and documented techniques.

As indicated above, the present invention, in particular, relates to a method of reprogramming a mature human fibroblast into a lineage-specific multi-potent neural precursor cell (FIG. 1B).

Generally, the step of delivering one or more selected factors to mature mammalian cells in the context of the present invention includes the delivery of factors such as, for example proteins or genes, by standard delivery techniques. These standard techniques have been described, for example in: "Viral Vectors for Gene Therapy—Methods and Protocols" Series: Methods in Molecular Medicine, Vol. 76, Machida, Curtis A. (Ed.) 2003, 608 p. 117; in Gene Therapy Protocols—Volume 2 "Design and Characterization of Gene Transfer Vectors" Series: Methods in Molecular Biology, Vol. 434, LeDoux, Joseph (Ed.) 3rd ed., 2008, XII, 314 p. 59; in Gene Delivery to Mammalian Cells, Volume 2 "Viral Gene Transfer Techniques" Series: Methods in Molecular Biology, Vol. 246, Heiser, William C. (Ed.) 2004, 592 p. 69; in Gene Delivery to Mammalian Cells Volume 1 "Nonviral Gene Transfer Techniques" Series: Methods in Molecular Biology, Vol. 245, Heiser, William C. (Ed.) 2004, 320 p. 36; and/or in "RNA Silencing—Methods and Protocols" Series: Methods in Molecular Biology, Vol. 309, Carmichael, Gordon (Ed.) 2005, 352 p. 74, all of which are herein incorporated by reference in their entirety.

The factors delivered to the mature mammalian cells can be selected from proteins such as transcription factors, nucleic acids encoding the transcription factors, small molecules capable of influencing the amount of the transcripton factors present in the somatic cell, or any combinations thereof.

The invention is further described by the following non-limiting examples.

EXAMPLE 1

Source and Maintenance of Adult Human Dermal Fibroblast (HDF) Cells

Mature human dermal fibroblast (HDF) cells, as a convenient model to exemplify the invention, were purchased from Cell Applications Inc, (San Diego, USA).

HDF cells were maintained in Fibroblast Growth Media (Cell Applications) with 2% heat-activated FBS (Invitrogen, USA), in accordance with manufacturer's instructions and common laboratory cell culture techniques and equipment.

EXAMPLE 2

Culture and Programming of Adult Human Dermal Fibroblast (HDF) Cells

After completing protein transduction (Example 4) or plasmid transfection (Example 5), HDF cells were harvested by trypsinization and transferred to either a 6-well (Nunc, Denmark) or a 24-well plate (Nunc) for proliferation. Approximately 3 days post-transfection or post-transduction, the cell media was changed to Neurobasal A (NBA) proliferation medium comprising Neurobasal-A (Invitrogen), 1% D-glucose (Sigma Aldrich), 1% Penicillin/Streptomycin/Glutamine (Invitrogen), 2% B27 supplement with Retinoic acid (Invitrogen), 0.2% EGF (Peprotech, USA), 0.08% FGF-2 (Peprotech), 0.2% Heparin (Sigma Aldrich, USA) and Valproic acid (Sigma Aldrich) to a concentration of 1 μM. The media was changed thrice weekly, and cells were replated regularly (2-8 times up to a maximum of weekly replating, becoming more regular as colonies began to develop) to remove non-reprogrammed cells until widespread colony formation was achieved.

EXAMPLE 3

Establishment and Optimisation of Protein Transduction Technique

Fluorescent R-phycoerythrin protein (PE) was either obtained from Oz Bioscience or Sigma-Aldrich. To optimise protein transduction 5×10$^4$ HDF cells were plated in 24-well plates 24 hrs before transduction. One hour before transduction Fibroblast Growth Media was removed and replaced by pre-warmed serum-free D-MEM. Fluorescent R-phycoerythrin protein (PE; 1 μg) was mixed with either ProDeliverIn (Oz Bioscience, France) or Proteofectene (Biontex, USA) in ratios of 1:1, 1:2 and 1:3 (m/v), incubated for 20 min to form complexes and added onto. HDF cells, respectively. The transduction medium was replaced with normal Fibroblast Growth Media after 3 hrs. To further optimise efficient protein transduction, HDF cells were also incubated with PE-protein transduction complexes for 48 hrs in normal Fibroblast Growth Media. Twenty-four hours post transduction, the uptake of PE was analysed by epifluorescence microscopy using a Nikon Eclipse TE2000U (Nikon) and flow cytometry analysis using a BD LSR-II (Becton Dickinson, USA). Control experiments were performed adding PE without the transduction reagent to the cells.

Results

Figure 2:
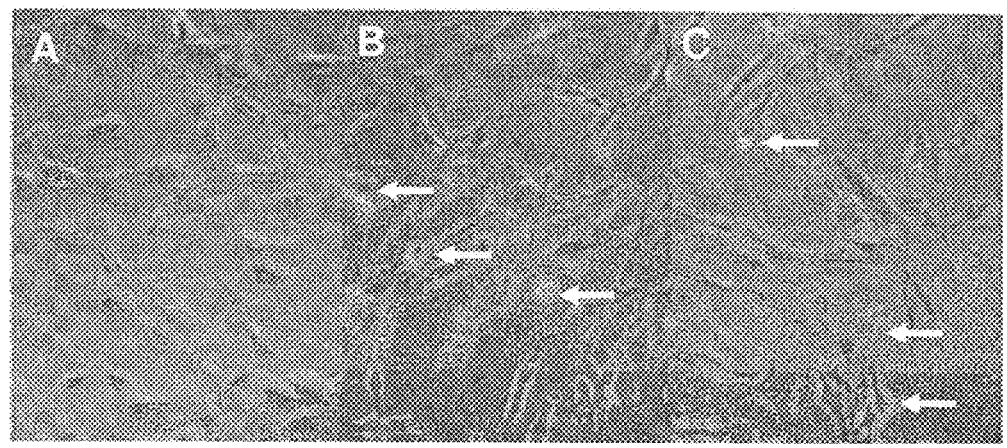
FIG. 2 is a series of epifluorescence images of phycoerythrin (PE) transduced cells using either the ProDeliverIn (B) or Proteofectene (C) transduction systems. PE fluorescent signal can be seen in both ProDeliverIn (B) and Proteofectene (C) transduced cells (arrows), while no intracellular PE fluorescent signal was observed in control experiments (A).

Protein transduction of mature HDFs using either ProDeliverIn or Proteofectene resulted in cellular uptake of fluorescent PE protein using a 1:2 ratio of protein to transduction reagent whereas no intracellular PE could be observed in control experiments adding PE without transduction reagent to the cells (FIG. 2A-C)

Figure 2D:
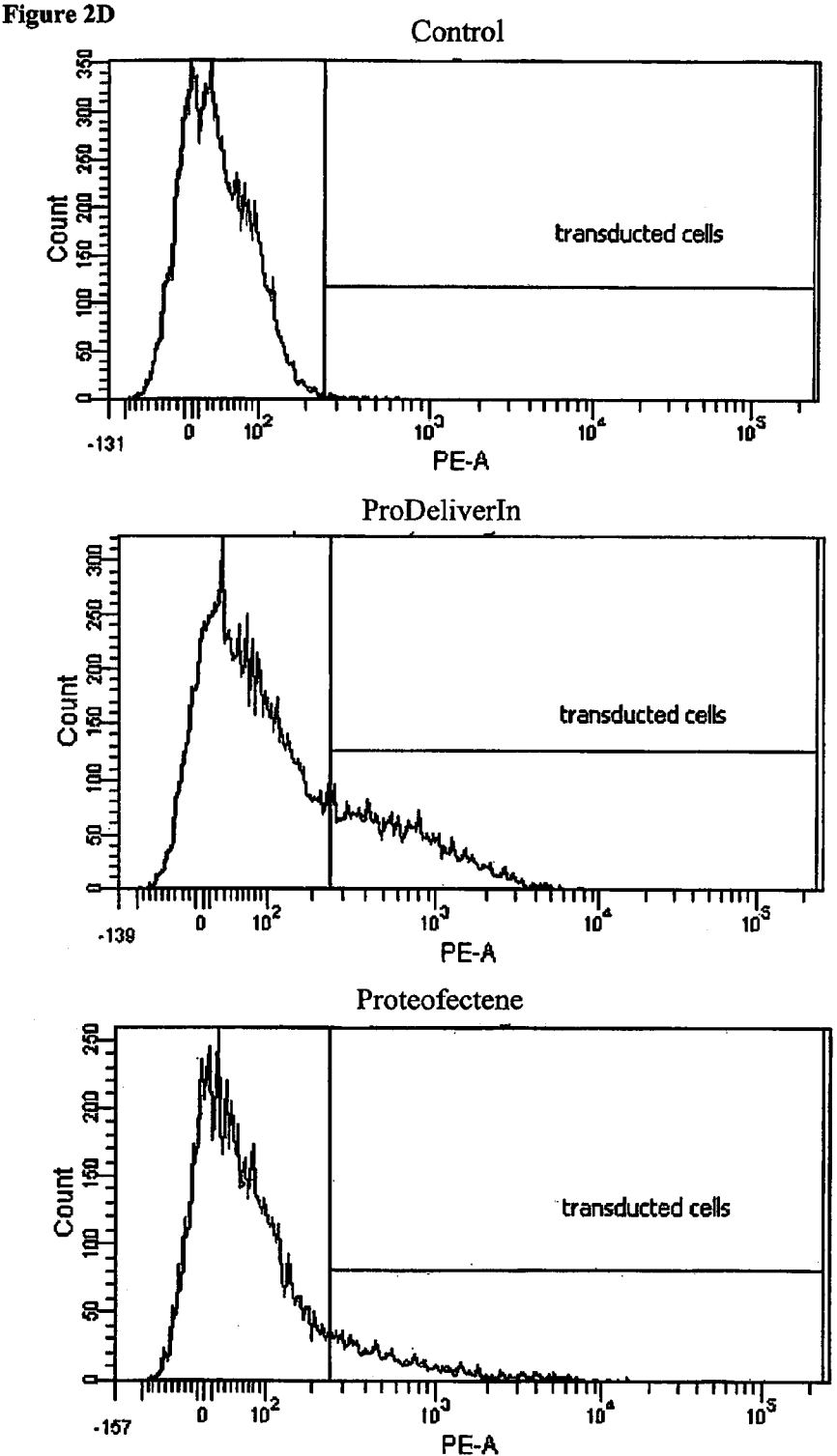
FIGS. 2(D) and (E) are series of fluorescence activated cell sorting (FACs) blots showing (D) the analysis of human dermal fibroblasts (HDF) transduced with PE using the ProDeliverIn and the Proteofectene system, while (E) shows FACs blots similar to the ones of FIG. 2(D) comparing PE and ProDeliverIn ratios of 1:1, 1:2 and 1:3.

FACS analysis revealed 23% cell transduction using the ProDeliverIn system compared to 13% cell transduction with the Proteofectene system when using 1 μg PE protein in a ratio of 1:2 (FIG. 2D).

Figure 2E:
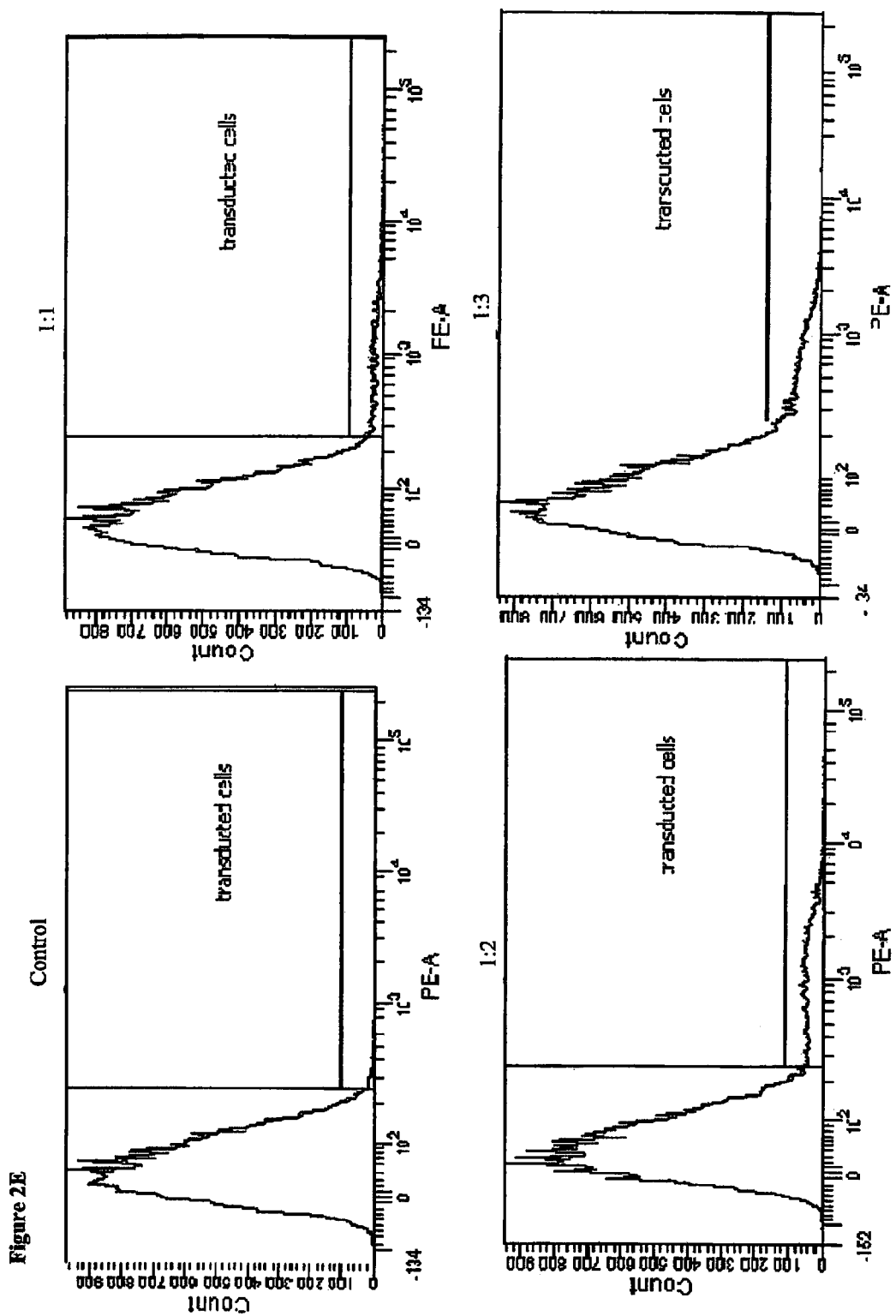
Figure 3:
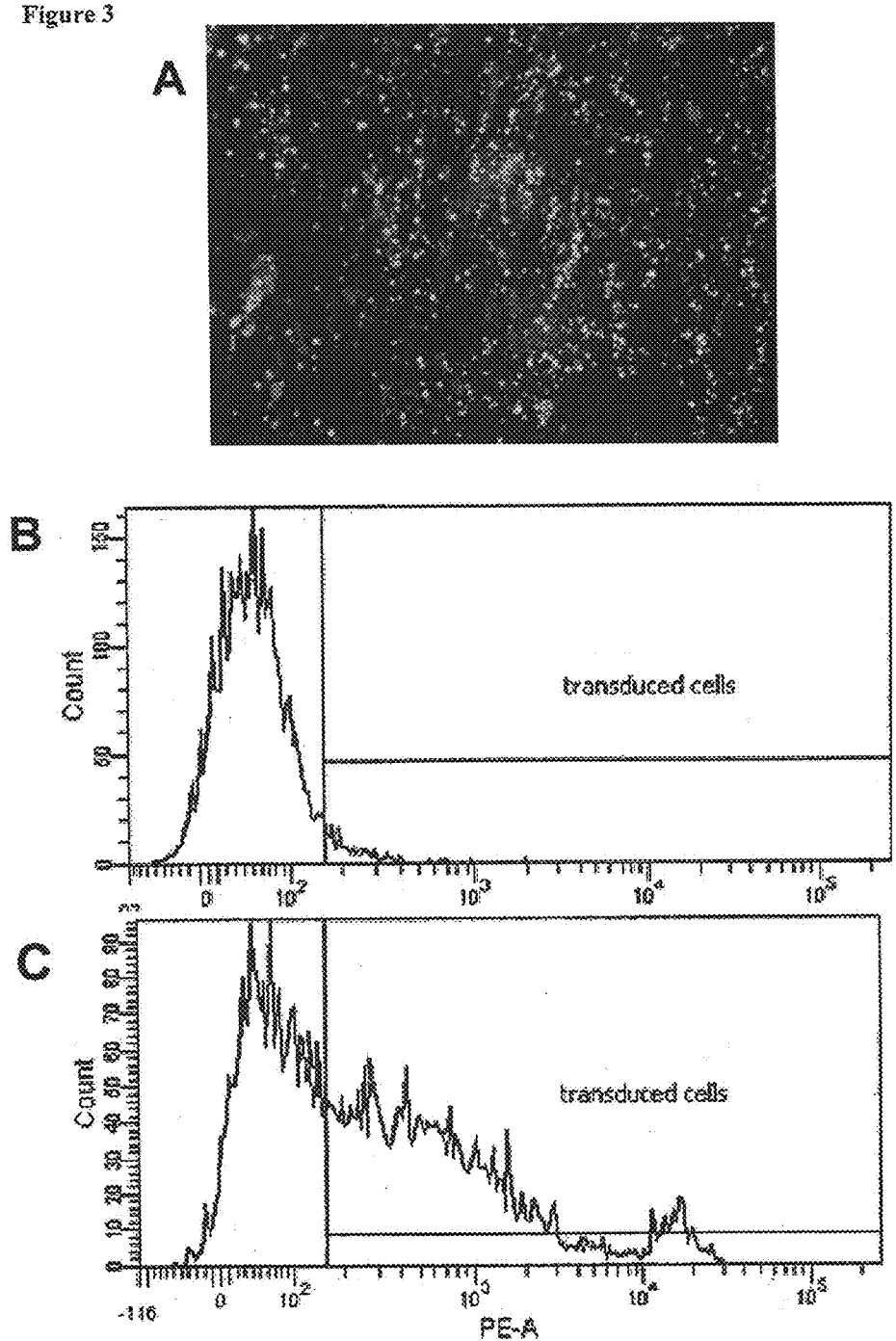
FIG. 3 is an epifluorescence image of phycoerythrin (PE) transduced cells using the ProDeliverIn transduction system (A).

When comparing different ratios of PE protein and ProDeliverIn, a 1:2 ratio resulted in the highest amount of 13% PE-positive cells compared to 6.5% with a ratio of 1:1 and 11% with a 1:3 ratio 48 hrs post transduction when 0.5 μg PE protein was applied and incubated for 3 hrs (FIG. 2E). Transduction efficiency could be improved to 54% PE-positive cells using the ProDeliverIn system by using 5 μg PE protein in a ratio of 1:2 and increasing incubation time to 48 hrs (FIGS. 3B and C). The cellular uptake of fluorescent PE protein (red) is shown in FIG. 3A.

EXAMPLE 4

Delivering Transcription Factors Via Protein Transduction

Recombinant Sox2-TAT protein was commercially obtained from Preprotech. Recombinant Pax6 protein was commercially obtained from Abnova. Co-transduction of Sox2-TAT (Peprotech) and Pax6 (Abnova, Taiwan) full-length proteins was performed by incubating mature HDFs at a density of 5×10$^5$ in uncoated coated six-well plates with 5 µg protein mixture and ProDeliverIn in a ratio 1:2 (m/v) for 48 hrs in Fibroblast Growth Media. After 48 hrs the protein transduction media was replaced with NBA proliferation media containing 1 µM valproic acid and cultured for further 24 hrs. Four protein transduction cycles were applied to the HDF cells before they were completely changed to NBA proliferation media containing 1 µM valproic acid. Media was changed every 2-3 days with weekly replating until widespread colonies were observed. The colonies were then isolated for PCR or immunocytochemical analysis (Examples 7 and 8).

EXAMPLE 5

Figure 4:
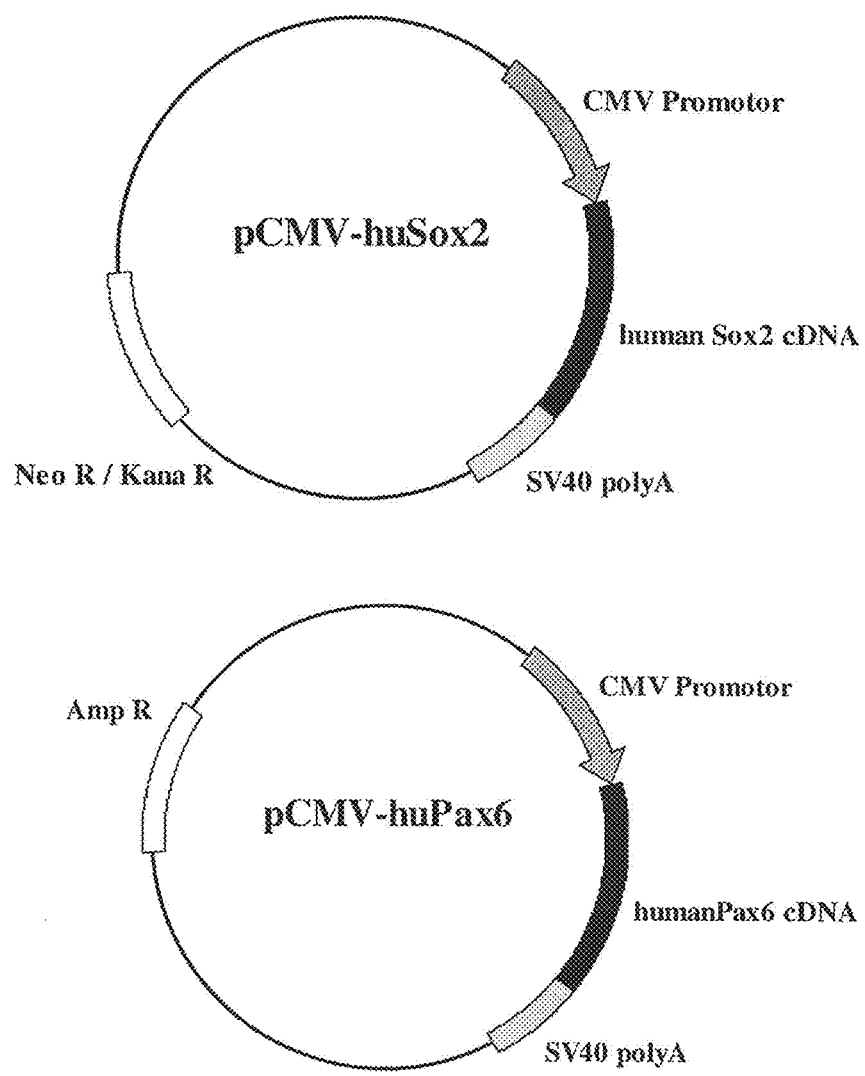
FIG. 4 shows schematic plasmid maps illustrating features of the pCMV-huSox2 and pCMV-huPax6 plasmids

Delivering Transcription Factors Via Plasmid Transfection cDNAs of Sox2 and Pax6 were purchased from Addgene and Invitrogen and cloned into pDNA backbones to be driven under the CMV promoter, respectively (see FIG. 4). The plasmids were amplified and purified using a PureLink HiPure Plasmid Filter Maxiprep Kit (Invitrogen). Transfections were performed with the Lipofectamine LTX reagent (Invitrogen), and 5×10$^5$ HDF cells, per well were seeded into uncoated 6-well plates 24 hr prior to the transfection. Gene transfer complexes were formed by mixing the Plus Reagent (Invitrogen) with 1 µg of each pDNA in Optimem medium (Invitrogen), then adding LTX gene delivery agent at a ratio of 6:1 (v/m). Cells were incubated with the transfection mixture for 5 hours, then were given fresh Fibroblast Growth media. After 3 days the cells were given NBA proliferation media containing 1 µM valproic acid. The media was changed every 2-3 days, with regular replating occurring until colonies were observed. The colonies were isolated for PCR and immunocytochemical analysis (Examples 7 and 8). Control experiments were performed using an eGFP control plasmid.

Results

Figure 5:
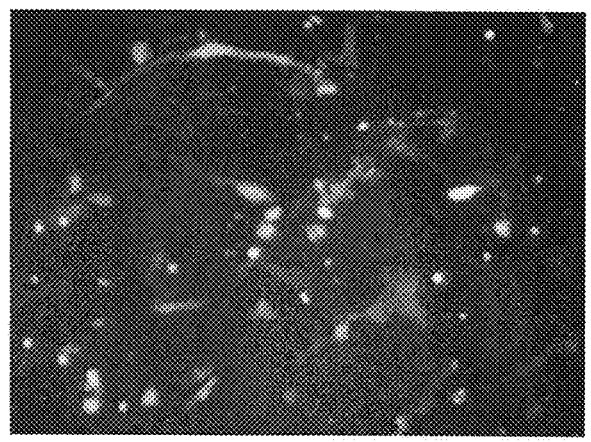
FIG. 5 is an epifluorescence image of Green Fluorescent Protein (eGFP) transduced HDF cells using the Lipofectamine LTX gene delivery agent (A).
Figure 5:
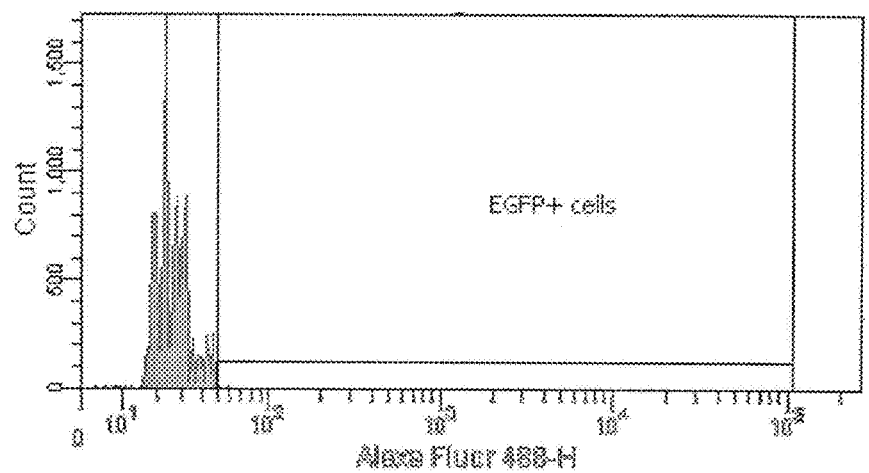
Figure 5:
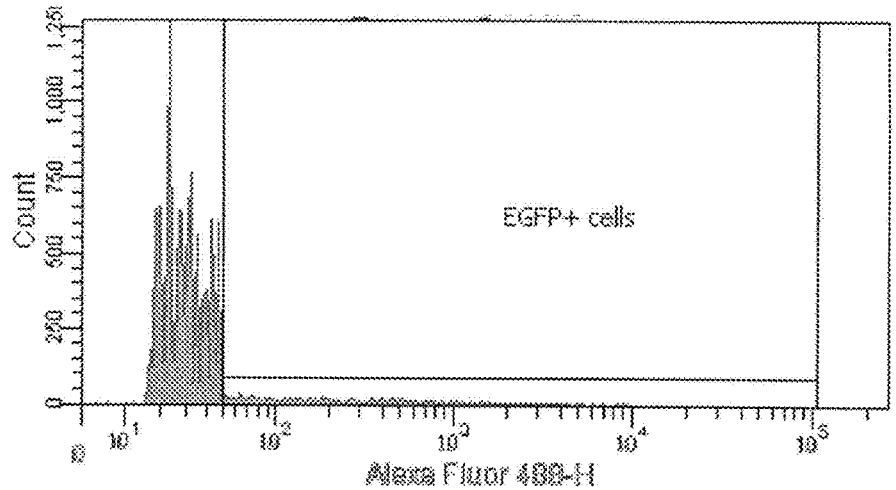

FACS analysis revealed that 12% of cells were transfected with eGFP (FIG. 5C) using LTX reagent as described, compared to 0% for untransfected cells (FIG. 5B). The cellular uptake of fluorescent eGFP plasmid (green) is shown in FIG. 5A.

EXAMPLE 6

Assessment of Colony Development and Proliferation of iMNP Cells

HDF cells were transfected as in Example 5 and switched to NBA proliferation media containing 1 µM valproic acid 3 days post-transfection and cultured as per Example 2. Colonies formed within 30 days. A cohort of colonies were then dissociated to 5-10 cell colonies by scraping and mechanical trituration to assess the ability of the colonies to self-renew and form secondary colonies. The dissociated colonies were replated onto uncoated 6 well plates (Nunc) and cultured in NBA proliferation media containing 1 µM valproic acid. The 5-10 cell colonies formed secondary colonies over a period of 14 days. The diameter (size) of the secondary colonies was measured and plotted as a percentage of measured colonies against 4 time points—pre-dissocation ("pre diss."), 6 days post-dissociation, 10 days post-dissociation and 14 days post-dissociation.

Results

Figure 6:
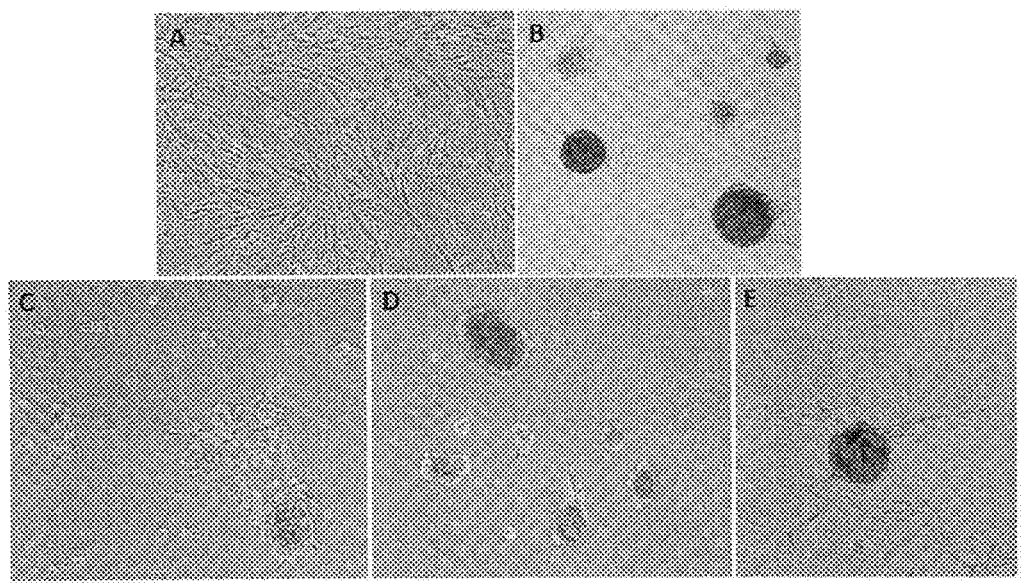
FIG. 6 are brightfield images of iMNP colony formation (A to E).
Figure 6:
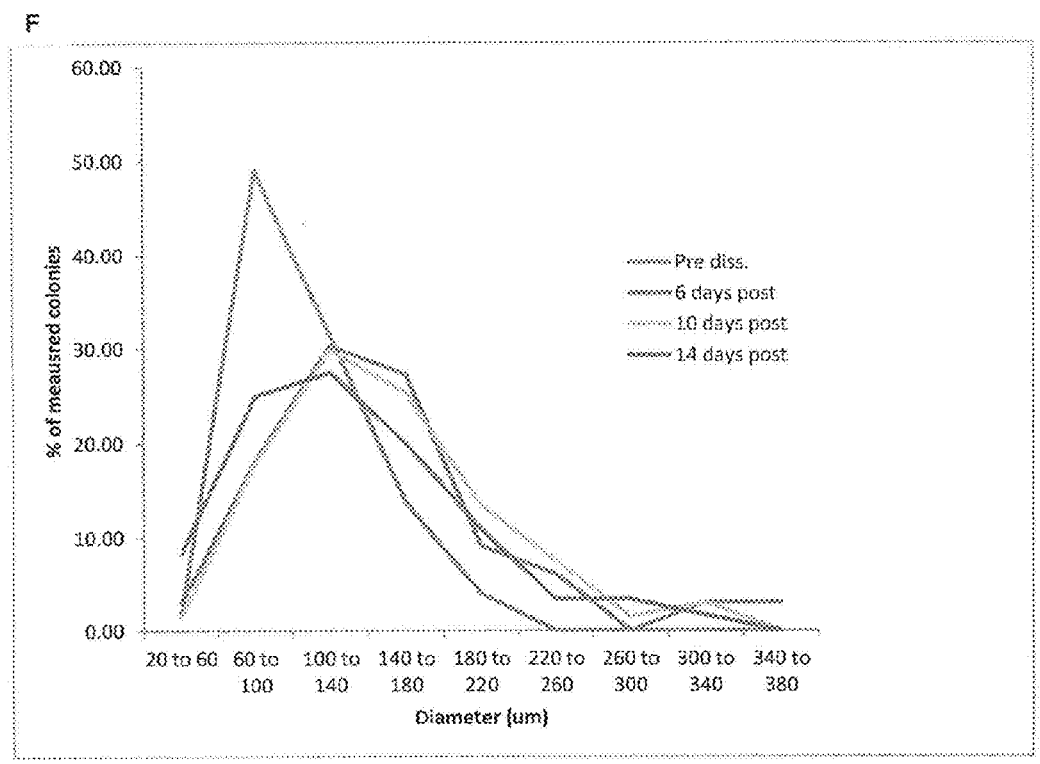

Primary iMNP colonies began to form within 7 days of Sox2/Pax6 transfection. Non-reprogrammed cells were removed by regular replating until widespread colony formation was achieved approximately 30 days following transfection (FIGS. 6A and B). Most importantly, colony formation did not require the presence of a feeder cell layer. We estimate an efficiency of colony formation at approximately 0.05% of total HDFs plated.

Induced MNP colonies formed from Sox2/Pax6 transfection also exhibited the ability to undergo self-renewal by the formation of secondary iMNP colonies from dissociated primary iMNP colonies. Secondary colonies developed by 4 to 6 days following dissociation of primary colonies (FIG. 6C to F). Both the number and size of the secondary colonies was increased compared to the primary colonies (FIG. 6F). Secondary iMNP colony formation appeared to plateau by 6 days following dissociation.

EXAMPLE 7

Characterisation of Mature Human Dermal Fibroblast Derived iMNP Cells by RT-PCR

Total RNA was isolated from iMNP cells and normal mature HDF cells using a PureLink RNA Mini Kit (Invitrogen). CDNA was produced from total RNA using a Superscript reverse transcriptase (Invitrogen) following the manufacturer's protocol. Expression of neural precursor cell and immature neuronal markers were detected by RT-PCR using a Taq DNA polymerase (New England) and the following primers listed in Table 1.

TABLE 1

| Oct 4: | |
|---|---|
| | [SEQ ID NO:1] |
| Oct4-FP | GTGAGAGGCAACCTGGAGAATT |
| | [SEQ ID NO:2] |
| Oct4-RP | CATTCCTAGAAGGGCAGGCACC |
| Sox1: | |
| | [SEQ ID NO:3] |
| Sox 1-FP | CAGTACAGCCCCATCTCCAAC |
| | [SEQ ID NO:4] |
| Sox 1-RP | GCGGGCAAGTACATGCTGA |
| Sox2: | |
| | [SEQ ID NO:5] |
| Sox2-FP | GCCGAGTGGAAACTTTTGTCG |
| | [SEQ ID NO:6] |
| Sox2-RP | GCAGCGTGTACTTATCCTTCTT |
| Sox3: | |
| | [SEQ ID NO:7] |
| Sox3-FP | CGCGGGTTCCTGCTGATTT |
| | [SEQ ID NO:8] |
| Sox3-RP | CGGGGTTCTTGAGTTCAGTCT |
| Pax6: | |
| | [SEQ ID NO:9] |
| Pax6-FP | TCACAGCGGAGTGAATCAGC |
| | [SEQ ID NO:10] |
| Pax6-RP | TATCGTTGGTACAGACCCCCTC |

TABLE 1-continued

Mash1:

| | | [SEQ ID NO:11] |
|---|---|---|
| Mash1-FP | GAATGGACTTTGGAAGCAG | |
| | | [SEQ ID NO:12] |
| Mash1-RP | AACTGGTTAGGATAGATACA | |

Hes1:

| | | [SEQ ID NO:13] |
|---|---|---|
| Hes1-FP | GCACAGAAAGTCATCAAAGCC | |
| | | [SEQ ID NO:14] |
| Hes1-RP | TTGATCTGGGTCATGCAGTTG | |

Hes5:

| | | [SEQ ID NO:15] |
|---|---|---|
| Hes5-FP | TTCTCAGAGAATGTGTGTGCAGAGT | |
| | | [SEQ ID NO:16] |
| Hes5-RP | GGTCAGACACTTGGCAGAAGATG | |

Ngn2:

| | | [SEQ ID NO:17] |
|---|---|---|
| Ngn2-FP | GCTGGCATCTGCTCTATTCC | |
| | | [SEQ ID NO:18] |
| Ngn2-RP | ATGAAGCAATCCTCCCTCCT | |

Results

Figure 7:
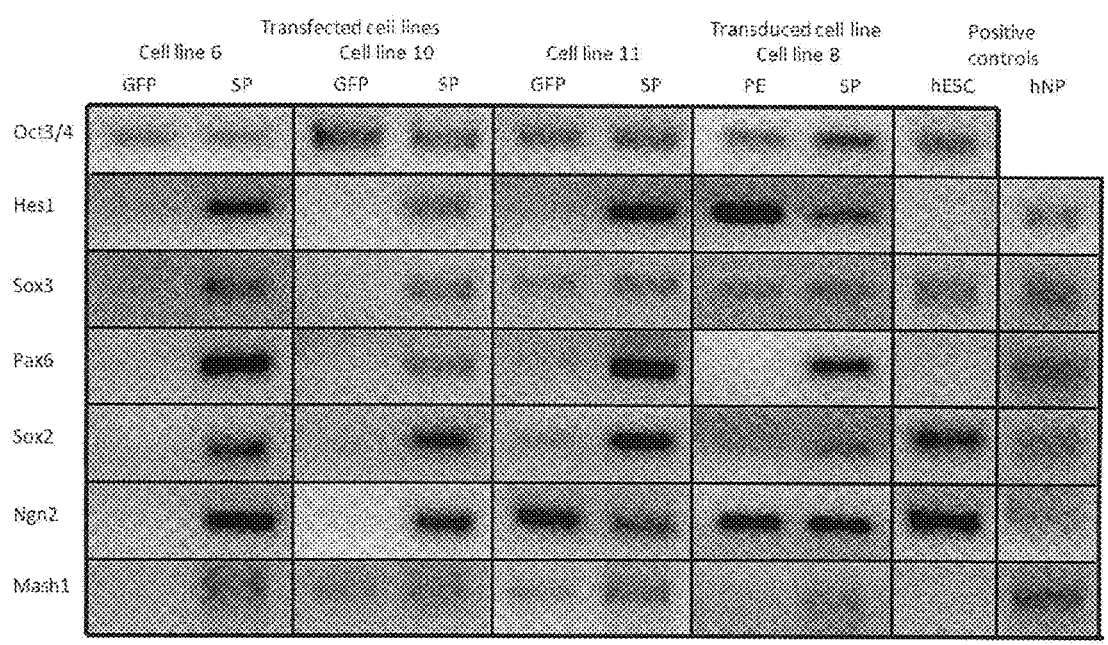
FIG. 7 is a RT-PCR panel demonstrating the expression of the neural precursor cell and immature neuronal marker genes Hes1, Sox3, Pax6, Sox2, Ngn2, and Mash1, and the pluripotency marker gene Oct3/4 in control (GFP or PE) and Sox2/Pax6 transfected or transduced iMNP colonies. Positive controls are samples from human embryonic stem cell cultures (hESC) and from human neural precursor cell cultures (hNP).

Sox2/Pax6 iMNP colonies consistently expressed a full range of the neural precursor cell genes Hes1, Sox3, Sox2, and Pax6 (FIG. 7). In addition, colonies were observed to express the immature neuronal markers Ngn2 and Mash1 (FIG. 7). The expression of neural precursor cell and immature neuronal marker genes was seen in colonies generated by either plasmid transfection or protein transduction. Expression of Hes1, Sox3, Sox2, Pax 6, Ngn2 or Mash1 was occasionally detected in control (GFP transfected or PE transduced) colonies (FIG. 7; cell line 11 and cell line 8). This may indicate that culture of adult HDF cells in NBA proliferation media containing 1 µM valproic acid alone may be sufficient to promote induction of neural precursor genes. However, it is apparent from the results presented in FIG. 7 that transfection or transduction of adult HDFs with Sox2 and Pax6 is required to consistently obtain induction of a wide range of neural precursor cell and immature neuronal marker genes.

FIG. 7 also demonstrates expression of the pluripotency gene Oct3/4 in both control and Sox2/Pax6 transduced or transfected colonies. Expression of Oct3/4 does not in itself indicate pluripotency of the resulting colonies but most likely demonstrates the expression of Oct3/4 in adult HDF cells (Zangrossi et al, (2007) *Stem Cells* 25: 11675-1680; Chin et al, (2009) *Biochemical and Biophysical Research Communications* 388: 247-251)

EXAMPLE 8

Characterisation of Immature Neuronal Cells from iMNP Cells by Immunocytochemistry Colonies were fixed in 4% paraformaldehyde and standard double-label fluorescent immunocytochemical procedures were performed using human-specific antibodies directed against the immature neuronal markers Mash1/Ashl1 (Chemicon), and Neurogenin2 (Chemicon, USA). DAPI was used as a counterstain for cell nuclei. Untreated HDF cells were used as a negative control. The standard fluorescent immunocytochemical procedures have, for example, been described in "Immunocytochemical Methods and Protocols" Series: Methods in Molecular Biology, Edited by Constance Oliver and Maria Célia Jamur, $3^{rd}$ edition, 2010 Humana Press, which is incorporated herein in its entirety.

Results

Figure 8:
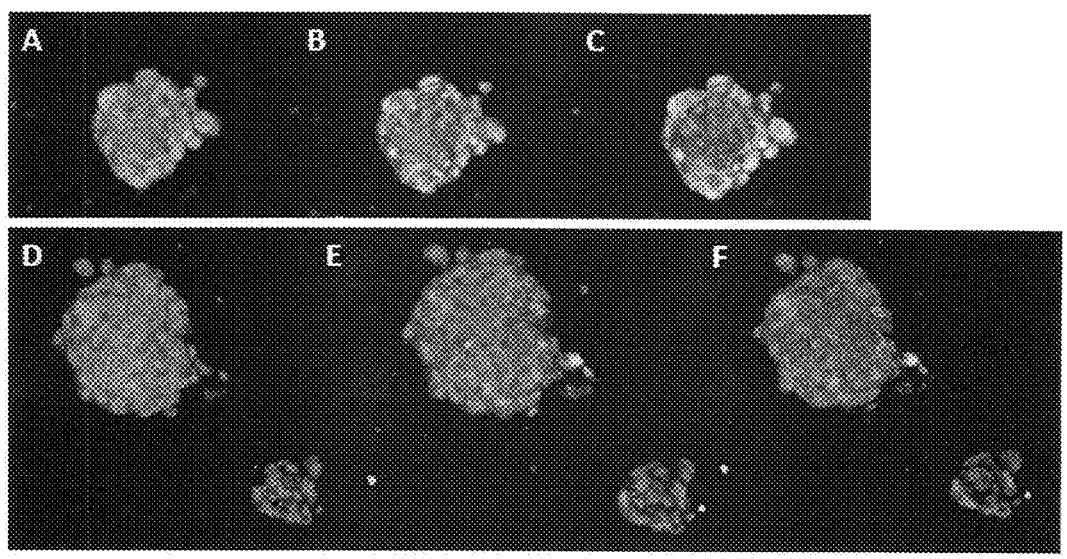
FIG. 8 are epifluorescence images of Sox2/Pax6 transfected iMNP colonies expressing the immature neuronal markers Mash1 (red; A and D) and Ngn2 (green; B and E). Images in (C and F) demonstrate co-expression of Mash1 (red) and Ngn2 (green). DAPI (blue) is used to detect individual cell nuclei (A, B, D and E).

A population of Sox2/Pax6 iMNP colonies were observed to express the immature neuronal markers Mash1 and Ngn2 (FIG. 8). As demonstrated in FIGS. 8C and F, individual cells within the colonies expressing Mash1 also expressed Ngn2. This indicates a population of cells within the iMNP colony have been reprogrammed towards an immature neuronal lineage.

Although the invention has been described by way of example, it should be appreciated that variations and modifications may be made without departing from the scope of the invention. Furthermore, where known equivalents exist to specific features, such equivalents are incorporated as if specifically referred to in this specification.

The claims defining the invention are as follows:

1. A method of reprogramming a mature mammalian fibroblast into a multi-potent neural precursor cell, said method comprising the steps of: a) delivering transcription factors consisting of Sox2 and Pax6 to said mature mammalian fibroblast via protein transduction or via protein expression from a transfected plasmid vector, wherein said transcription factors, in combination, induce conversion of said mature mammalian fibroblast into a multi-potent neural precursor cell; and b) culturing said mature mammalian fibroblast from step a) in medium supporting growth of said multi-potent neural precursor cell.

2. The method according to claim 1 wherein said mature mammalian fibroblast is selected from the group consisting of lung fibroblasts, kidney fibroblasts, cardiac fibroblasts, stromal fibroblasts, foreskin fibroblasts and dermal fibroblasts.

3. The method according to claim 1 wherein said mature mammalian fibroblast is a mature human dermal fibroblast.

4. The method according to claim 1 wherein said mature mammalian fibroblast is a cell from a patient suffering from a neurological disorder or injury in which tissue regeneration is a component of healing and wherein said multi-potent neural precursor cell is a disease-specific multi-potent neural precursor cell.

5. The method of claim 4 wherein said multi-potent neural precursor cell expresses at least one neural cell lineage marker selected from the group consisting of Pax6, Sox2, Hes 1, Hes 5, Sox1, Sox3, Mash 1/Ashl 1 and neurogenin 2.

6. The method according to claim 1 wherein said medium is supplemented with a chromatin modifying agent that facilitates reprogramming of said mature mammalian fibroblast and wherein said chromatin modifying agent is selected from the group consisting of an agent that promotes acetylation of chromatin, an agent that inhibits deacetylation of chromatin, an agent that that alters histone methylation states within chromatin and an agent that induces DNA demethylation within chromatin.

7. The method according to claim 6 wherein said chromatin modifying agent is valproic acid at 1 μM.

8. The method according to claim 7 wherein the valproic acid is used at a concentration of 1 μM.

9. The method according to claim 1 wherein said mature mammalian fibroblast is a mature human dermal fibroblast and wherein said mature human dermal fibroblast is from a patient suffering from a neurological disorder or injury in which tissue regeneration is a component of healing and wherein said reprogrammed multi-potent neural precursor cell is a disease-specific reprogrammed multi-potent neural precursor cell.

* * * * *